(12) United States Patent
Bechtel et al.

(10) Patent No.: US 12,702,455 B2
(45) Date of Patent: Aug. 11, 2026

(54) SCREW TOWER AND ROD REDUCTION TOOL

(71) Applicant: GLOBUS MEDICAL, INC., Audubon, PA (US)

(72) Inventors: Matthew Bechtel, Philadelphia, PA (US); Caelan Allen, Ambler, PA (US); Neil R. Crawford, Chandler, AZ (US); Thomas Calloway, Pelham, NH (US); Steven Chang, Phoenix, AZ (US); Norbert Johnson, North Andover, MA (US); Jeffrey Forsyth, Cranston, RI (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 19/192,573

(22) Filed: Apr. 29, 2025

(65) Prior Publication Data

US 2025/0255649 A1 Aug. 14, 2025

Related U.S. Application Data

(63) Continuation of application No. 17/821,939, filed on Aug. 24, 2022, now Pat. No. 12,310,634, which is a continuation of application No. 17/382,782, filed on Jul. 22, 2021, now Pat. No. 11,439,444.

(51) Int. Cl.

| | |
|---|---|
| ***A61B 17/70*** | (2006.01) |
| ***A61B 17/00*** | (2006.01) |
| ***A61B 34/20*** | (2016.01) |

(52) U.S. Cl.
CPC ........ *A61B 17/708* (2013.01); *A61B 17/7082* (2013.01); *A61B 17/7083* (2013.01); *A61B 17/7085* (2013.01); *A61B 17/7086* (2013.01); *A61B 17/7091* (2013.01); *A61B 2017/00477* (2013.01); *A61B 34/20* (2016.02); *A61B 2034/2055* (2016.02); *A61B 2034/2065* (2016.02)

(58) Field of Classification Search
CPC .............. A61B 17/708; A61B 17/7082; A61B 17/7083; A61B 17/7085; A61B 17/7086; A61B 17/7091; A61B 34/20; A61B 2034/2055; A61B 2034/2065; A61B 2017/00477
See application file for complete search history.

(56) References Cited

U.S. PATENT DOCUMENTS

| | | |
|---|---|---|
| 2009/0143828 A1 | 6/2009 | Stad et al. |
| 2015/0066089 A1 | 3/2015 | Nelson et al. |
| 2017/0252074 A1 | 9/2017 | Semingson et al. |
| 2019/0125417 A1 | 5/2019 | Fischer |

FOREIGN PATENT DOCUMENTS

| | | |
|---|---|---|
| CN | 109069192 A | 12/2018 |
| CN | 212438798 U | 2/2021 |

*Primary Examiner* — Ellen C Hammond

(57) ABSTRACT

A system includes a screw tower, an instrument, and a housing. The instrument includes a driver shaft extendable longitudinally through the screw tower, and a threaded sleeve mounted on a proximal portion of the driver shaft. The housing includes one or more retention members coupleable to the screw tower, and a threaded button threadably coupleable to the threaded sleeve. The threaded sleeve is rotatable about a longitudinal axis to urge the driver shaft longitudinally relative to the screw tower.

17 Claims, 14 Drawing Sheets

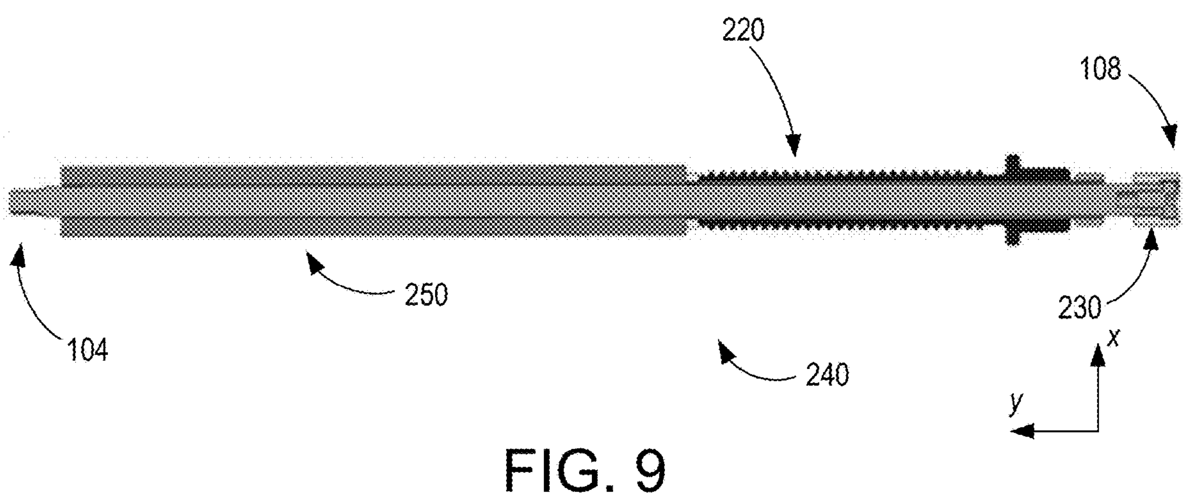
FIG. 9
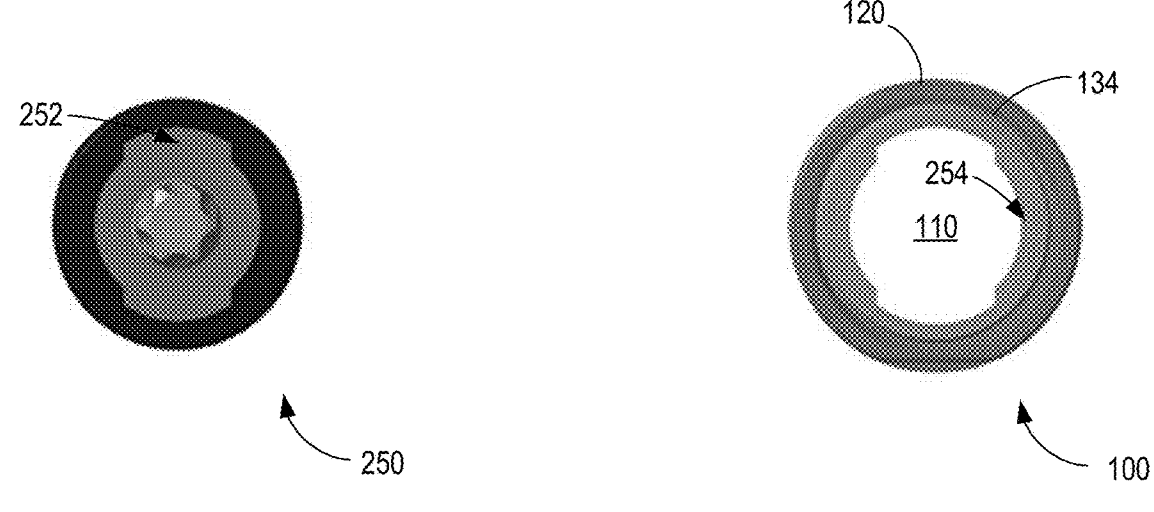
FIG. 10
FIG. 11

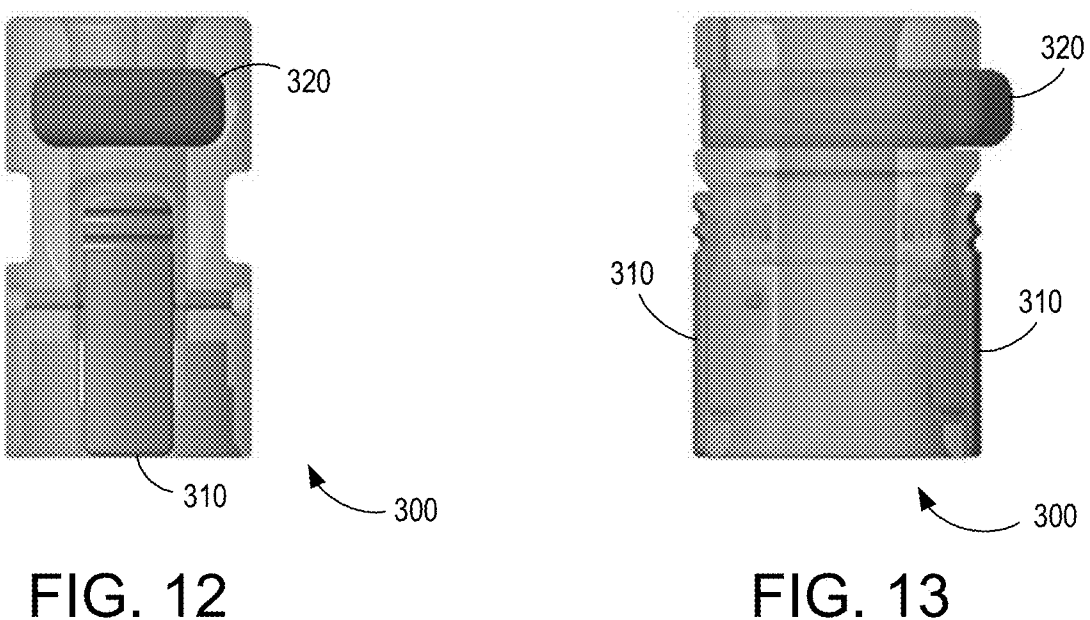
FIG. 12
FIG. 13
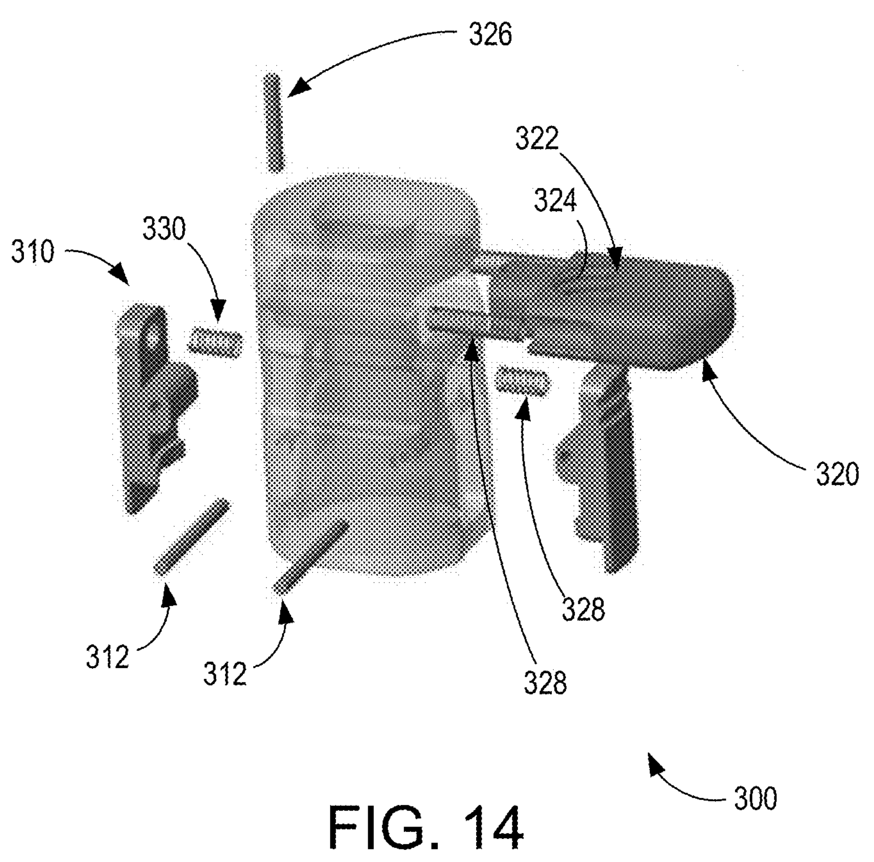
FIG. 14

502
502
512
512
500
510

502
502
512
512
510
500

SCREW TOWER AND ROD REDUCTION TOOL

CROSS-REFERENCE TO RELATED APPLICATION(S)

This application is a continuation of U.S. patent application Ser. No. 17/821,939 filed on Aug. 24, 2022, which is a continuation of U.S. patent application Ser. No. 17/382,782 filed on Jul. 22, 2021, the contents of which are incorporated by reference herein in its entirety for all purposes.

BACKGROUND

Spinal fixation devices may be anchored to specific portions of the vertebra. Such spinal fixation devices may include, for example, a shank portion coupleable to a vertebra, and a head portion having a receiving element. A fixation rod may be seated through the receiving element and locked in place by tightening the head portion. While known spinal fixation systems have proven effective, some rod reducers may be difficult, tiresome, and/or time-consuming to use.

SUMMARY

According to some examples of the inventive concepts described herein, a system may be provided to provide a rod reduction tool. The system includes a screw tower, an instrument, and a housing. The instrument includes a driver shaft extendable longitudinally through the screw tower, and a threaded sleeve mounted on a proximal portion of the driver shaft. The housing includes one or more retention members coupleable to the screw tower, and a threaded button threadably coupleable to the threaded sleeve. The threaded sleeve is rotatable about a longitudinal axis to urge the driver shaft longitudinally relative to the screw tower.

According to other examples of the inventive concepts described herein, a method may be provided to provide a rod reduction tool. The method includes extending a driver shaft longitudinally through a screw tower, mounting a threaded sleeve on a proximal portion of the driver shaft, coupling a housing to the screw tower using one or more retention members, and threadably coupling the housing to the threaded sleeve using a threaded button such that the threaded sleeve is rotatable about a longitudinal axis to urge the driver shaft longitudinally relative to the screw tower.

This summary is provided to introduce a selection of inventive concepts in a simplified form that are further described below in the detailed description. Other methods and related systems, and corresponding methods and computer program products, according to examples of the inventive subject matter will be or become apparent to one with skill in the art upon review of the following detailed description and the accompanying drawings. This summary is not intended to identify key features or essential features of the claimed subject matter, nor is it intended to be used as an aid in determining the scope of the claimed subject matter.

BRIEF DESCRIPTION OF THE DRAWINGS

The accompanying drawings, which are included to provide a further understanding of the disclosure and are incorporated in and constitute a part of this application, illustrate certain non-limiting examples of inventive concepts. In the drawings:

FIG. 9 is a cross-sectional view of another example instrument that may be used with a screw tower, such as the screw tower shown in FIG. 1 or 5;

FIG. 10 is a distal end view of the instrument shown in FIG. 9;

FIG. 11 is a proximal end view of an example screw tower, such as the screw tower shown in FIG. 1 or 5;

FIG. 12 is a partially transparent side view of an example housing that may be used with a screw tower, such as the screw tower shown in FIG. 1 or 5, and/or an instrument, such as the instrument shown in FIG. 7 or 9;

FIG. 13 is a partially transparent front view of the housing shown in FIG. 12;

FIG. 14 is a partially transparent, exploded perspective view of the housing shown in FIG. 12;

Figure 1:
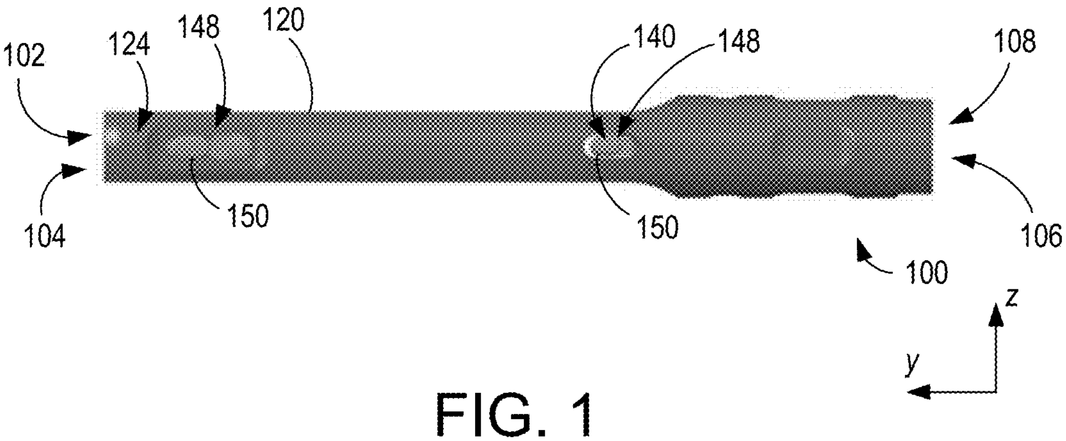
FIG. 1 is a side view of an example screw tower.

The drawings, which are not necessarily to scale, depict selected examples and are not intended to limit the scope of the disclosure. Although specific features of various examples of the disclosure may be shown in some drawings and not in others, this is for convenience only. The following detailed description is to be read with reference to the drawings, in which like elements in different figures have like reference characters.

DETAILED DESCRIPTION

The present disclosure relates to medical devices and, more particularly, to a screw tower and rod reduction tool. Examples described herein include a screw tower, an instrument, and a housing. The instrument includes a driver shaft extendable longitudinally through the screw tower, and a threaded sleeve mounted on a proximal portion of the driver shaft. The housing includes one or more retention members coupleable to the screw tower, and a threaded button threadably coupleable to the threaded sleeve. The threaded sleeve is rotatable about a longitudinal axis to urge the driver shaft longitudinally relative to the screw tower. The examples described herein enable a screw tower to be affixed, a fixation rod to be reduced, and/or a locking cap to be inserted in an efficient, user-friendly, and/or effective manner. While the examples described herein are described with respect to pedicle screws, one of ordinary skill in the art would understand and appreciate that the example systems and methods may be used with other types of fastening mechanisms.

Turning now to the drawings, FIGS. 1-4 show an example screw tower 100 that may be used to hold or engage a screw (e.g., a pedicle screw) for implantation of the screw via a minimally-invasive incision. The screw tower 100 may include, for example, an elongated tube defining a distal opening 102 for receiving the screw at a distal end 104, a proximal opening 106 for receiving one or more instruments, rods, implants, etc. at a proximal end 108, and a channel 110 extending longitudinally (e.g., along a Y-axis) therebetween.

In some examples, the screw tower 100 includes an outer sleeve 120 sized, shaped, and/or configured to engage a portion of the screw. For example, the outer sleeve 120 may include a first wall 122 and a second wall 124 opposing the first wall 122 such that a head feature of the screw (e.g., a lip of a tulip) may be positioned transversely therebetween. In some examples, the first wall 122 and/or second wall 124 may be cantilevered such that the outer sleeve 120 may be coupled to the screw using a cantilever snap-fit engagement. For example, as the head feature of the screw is urged in a proximal direction (e.g., in a negative Y-direction) toward the distal end 104 of the outer sleeve 120, the first wall 122 and/or second wall 124 may deflect or spread apart to allow the head feature to move in the proximal direction therebetween and return or snap back to a neutral configuration when the head feature clears a portion 126 of the first wall 122 and/or second wall 124 (e.g., a ridge or lip) such that the portion 126 of the first wall 122 and/or second wall 124 is disposed in an undercut and/or opening defined by the head feature of the screw. Alternatively, the outer sleeve 120 may engage or be coupled to the screw using any arrangement or mechanism that provides a quick, robust, and reliable connection. For example, in some examples, the outer sleeve 120 may be selectively rotated to couple the screw tower 100 to the screw by positioning the portion 126 of the first wall 122 and/or second wall 124 in the undercut or opening defined by the head feature of the screw and/or uncouple the screw tower 100 from the screw by spacing the portion 126 of the first wall 122 and/or second wall 124 from the undercut or opening defined by the head feature of the screw.

Figure 3:
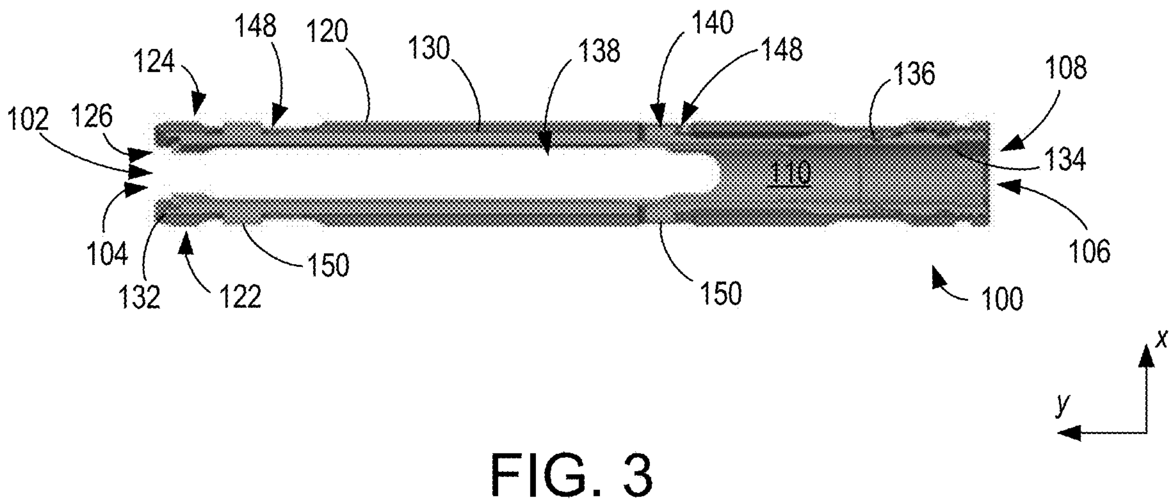
FIG. 3 is a cross-sectional view of the screw tower shown in FIG. 1.
Figure 4:
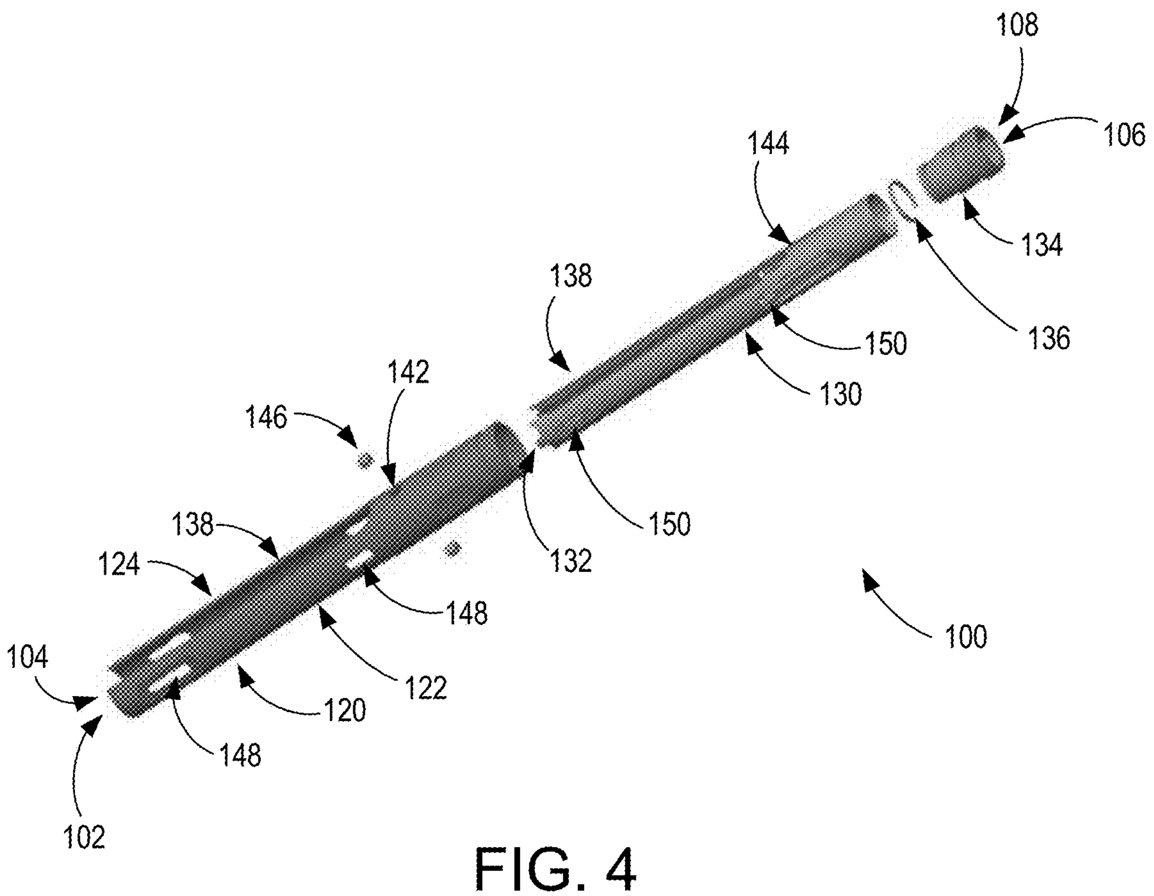
FIG. 4 is an exploded perspective view of the screw tower shown in FIG. 1.

As shown at FIGS. 3 and 4, the screw tower 100 may include an inner sleeve 130 coaxial with the outer sleeve 120. In some examples, the inner sleeve 130 may be sized, shaped, and/or configured to engage a portion of the screw coupled to the outer sleeve 120 at the distal end 104 thereof for "locking" or rigidly securing the screw in place relative to the screw tower 100. For example, when the inner sleeve 130 is moved or urged in a distal direction (e.g., in a positive Y-direction) while the outer sleeve 120 is coupled to the screw, the head feature may be clamped longitudinally between a mating portion 132 of the inner sleeve 130 (e.g., a tab or protrusion) and the portion 126 of the first wall 122 and/or second wall 124. In some examples, the mating portion 132 of the inner sleeve 130 may include one or more mating features that are sized, shaped, and/or configured to be received in one or more indented features and/or openings at the head of the screw. Additionally or alternatively, the mating portion 132 of the inner sleeve 130 may include one or more mating features that are sized, shaped, and/or configured to receive one or more tabs and/or protrusions at the head of the screw.

Figure 2:
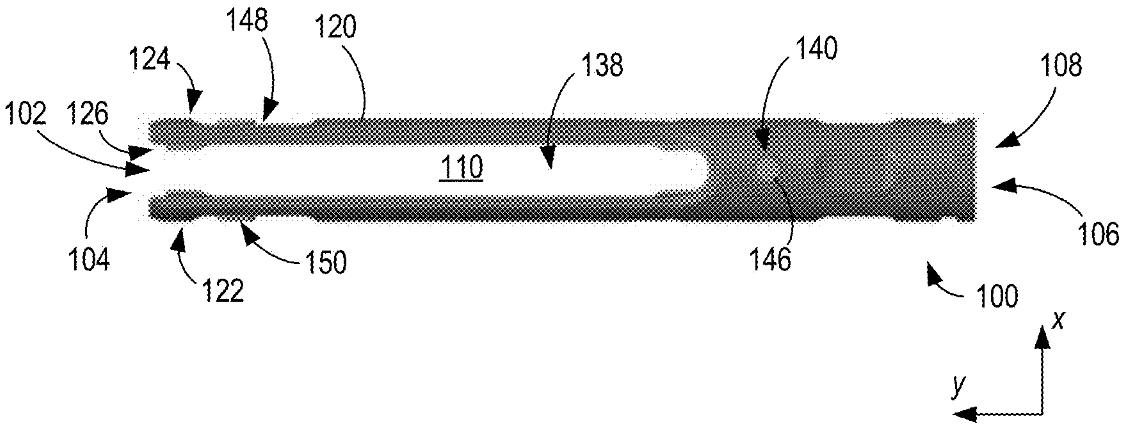
FIG. 2 is a front view of the screw tower shown in FIG. 1.

In some examples, an inner nut 134 may be used to move or urge the inner sleeve 130 longitudinally relative to the outer sleeve 120. As shown in FIGS. 3 and 4, the nut 134 may be threadably coupled to the outer sleeve 120 such that the nut 134 may be rotated about the longitudinal axis in a first direction (e.g., a clockwise direction) to move in the distal direction and/or in a second direction opposite the first direction (e.g., a counterclockwise direction) to move in the proximal direction (e.g., in a negative Y-direction). In some examples, a retaining clip or ring 136 may be used to couple the inner sleeve 130 to the nut 134 such that the inner sleeve 130 and nut 134 are prevented or restricted from moving longitudinally relative to each other while being free to rotate relative to each other. In this manner, the nut 134 may be selectively rotated to longitudinally translate the inner sleeve 130 relative to the outer sleeve 120. A relative orientation of the outer sleeve 120 and inner sleeve 130 may be maintained, for example, to ensure that the screw tower 100 includes one or more longitudinal channels 138 defined therein. For example, as shown in FIGS. 2, 3, and 4, channels 138 may be defined circumferentially between the first wall 122 and second wall 124 of the outer sleeve 120 (e.g., along a circumference of the outer sleeve 120). Channels 138 defined in the outer sleeve 120 may be aligned with channels 138 defined in the inner sleeve 130 to allow one or more rods to extend transversely through the screw tower 100. In some examples, channels 138 may be open at the distal end 104 of the outer sleeve 120 and/or inner sleeve 130 such that one or more transversely-extending rods may be received at the distal end 104 of the screw tower 100 and translated proximally (e.g., in a negative Y-direction) through the channels 138.

The screw tower 100 may include one or more control features 140 for controlling a relative movement between the outer sleeve 120 and inner sleeve 130. In some examples, the control features 140 may restrict an amount or degree of allowable movement between the outer sleeve 120 and inner sleeve 130. For example, the control features 140 may include one or more openings 142 defined in the outer sleeve 120, one or more longitudinal slots 144 defined in the inner sleeve 130, and one or more pins 146 extendable through the openings 142 and/or longitudinal slots 144. The openings 142 may be sized, shaped, and/or configured such that, when the pins 146 are extended therethrough, the outer sleeve 120 is restricted or prevented from moving rotationally (e.g., about the Y-axis) or longitudinally (e.g., along the Y-axis) relative to the pins 146. The longitudinal slots 144 may be sized, shaped, and/or configured such that, when the pins 146 are extended therethrough, the inner sleeve 130 is restricted or prevented from moving rotationally (e.g., about the Y-axis) relative to the pins 146 while being free to move longitudinally (e.g., along the Y-axis) relative to the pins 146 a length of the longitudinal slots 144. For another example, the control features 140 may include one or more longitudinal slots 148 defined in the outer sleeve 120 and one or more tabs and/or protrusions 150 of the inner sleeve 130 that are configured to extend radially outward through the longitudinal slots 148. The longitudinal slots 148 may be sized, shaped, and/or configured such that, when the protrusions 150 are extended therethrough, the outer sleeve 120 is restricted or prevented from moving rotationally (e.g., about the Y-axis) relative to the protrusions 150 while being free to move longitudinally (e.g., along the Y-axis) relative to the protrusions 150 a length of the longitudinal slots 148.

In some examples, the control features 140 may be selectively disengaged to allow a relative movement between the outer sleeve 120 and inner sleeve 130. For example, the pins 146 may be extracted or removed from the openings 142 defined in the outer sleeve 120 and the longitudinal slots 144 defined in the inner sleeve 130 such that walls defining the openings 142 and/or longitudinal slots 144 do not engage the pins 146 when the outer sleeve 120 and/or inner sleeve 130 is moved. For another example, the first wall 122 and/or second wall 124 of the outer sleeve 120 may be deflected or spread apart such that the protrusion 150 at a distal portion of the inner sleeve 130 is extracted or removed from the longitudinal slot 148 at a distal portion of the outer sleeve 120 and, thus, does not engage the first wall 122 and/or second wall 124 when the outer sleeve 120 and/or inner sleeve 130 is moved. For yet another example, the protrusion 150 at a proximal portion of the inner sleeve 130 is moved or urged radially inward such that the protrusion 150 is extracted or removed from the longitudinal slot 148 at a proximal portion of the outer sleeve 120 and, thus, does not engage the first wall 122 and/or second wall 124 when the outer sleeve 120 and/or inner sleeve 130 is moved. In some examples, a separate tool may be used to selectively disengage one or more control features 140 to allow the screw tower 100 to be at least partially disassembled (e.g., for sterilization and/or cleaning).

Figures 5, 6:
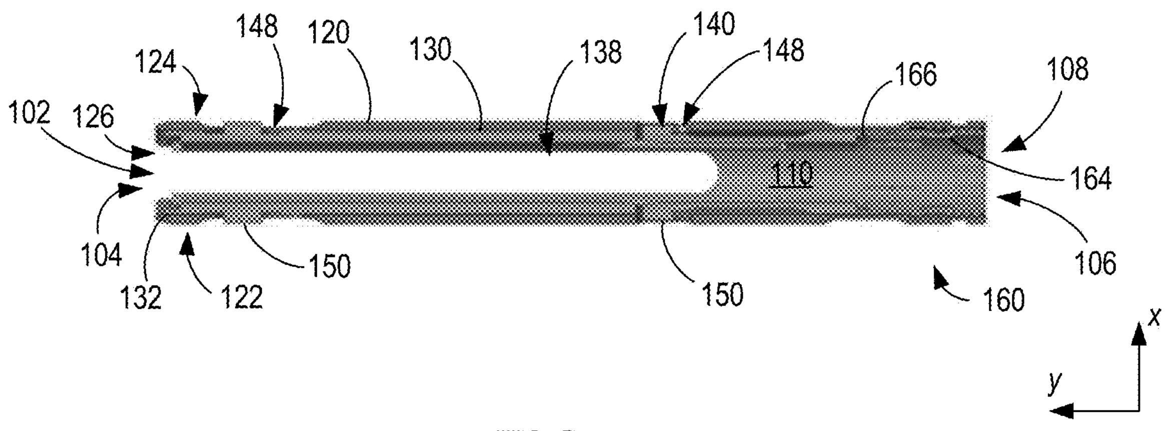
FIG. 5 is a cross-sectional view of another example screw tower.
FIG. 6 is an exploded perspective view of the screw tower shown in FIG. 5.

FIGS. 5 and 6 show another example screw tower 160 that may be used to hold or engage a screw for implantation of the screw via a minimally-invasive incision. As can be understood from a comparison of FIGS. 3 and 4 with FIGS. 5 and 6, the screw tower 160 shown in FIGS. 5 and 6 is substantially similar to the screw tower 100 shown in FIGS. 3 and 4, except the screw tower 160 includes an inner nut 164 (e.g., inner nut 134) having a compressible ledge 166. The compressible ledge 166 is configured to engage an inner surface of the inner sleeve 130 such that the inner sleeve 130 and nut 164 are prevented or restricted from moving longitudinally relative to each other while being free to rotate relative to each other. In this manner, the nut 164 shown in FIGS. 5 and 6 is selectively rotatable to longitudinally translate the inner sleeve 130 relative to the outer sleeve 120. As shown in FIGS. 5 and 6, the nut 164 may be threadably coupled to the outer sleeve 120 such that the nut 164 may be rotated about the longitudinal axis in a first direction (e.g., a clockwise direction) to move or urge the inner sleeve 130 in the distal direction and/or in a second direction opposite the first direction (e.g., a counterclockwise direction) to move or urge the inner sleeve 130 in the proximal direction (e.g., in a negative Y-direction).

Figure 7:
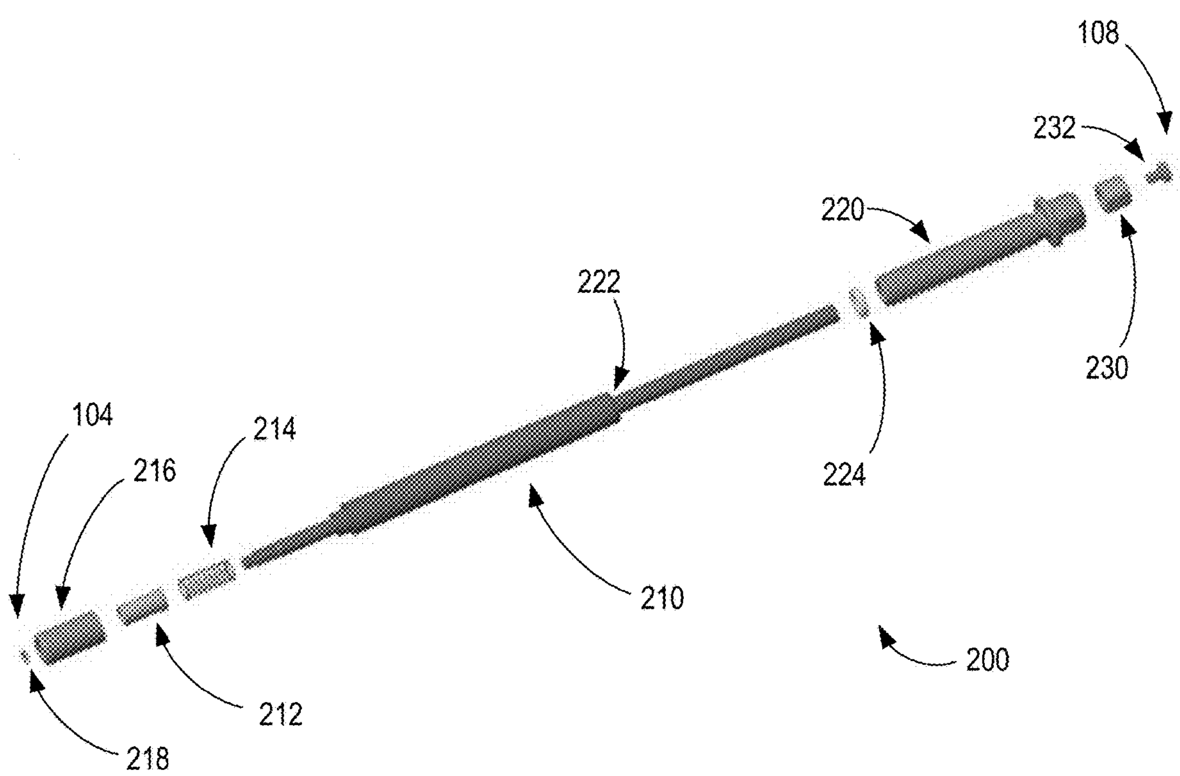
FIG. 7 is a side view of an example instrument that may be used with a screw tower, such as the screw tower shown in FIG. 1 or 5.
Figure 8:
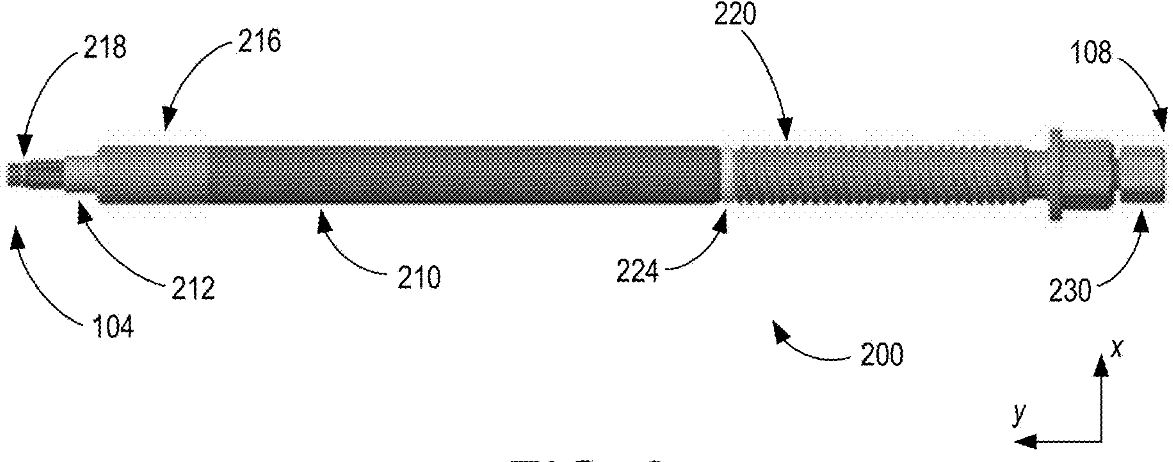
FIG. 8 is an exploded perspective view of the instrument shown in FIG. 7.

FIGS. 7 and 8 show an instrument 200 that may be used to reduce a rod and/or insert a locking cap on a screw. The screw may include or be coupled to a tulip on which the rod may be positioned, and the locking cap may be used to secure the rod within the tulip. The instrument 200 may be extended longitudinally between the proximal end 108 and the distal end 104 and/or used with the screw tower 100 (shown in FIGS. 1-4). In some examples, the instrument 200 includes a driver or inner shaft 210 sized, shaped, and/or configured to push or drive a rod extending transversely through the longitudinal channels 138 of the screw tower 100 in a distal direction (e.g., in a positive Y-direction). The rod may be pushed or driven, for example, by extending the inner shaft 210 through the channel 110 of the screw tower 100 to position the distal end 104 of the inner shaft 210 at or adjacent to the rod and moving or urging the inner shaft 210 in the distal direction.

As shown in FIGS. 7 and 8, a cap pusher 212 may be mounted on or coupled to a distal portion of the inner shaft 210. The cap pusher 212 may be sized, shaped, and/or configured to engage the locking cap and provide a force to the locking cap such that the locking cap may be coupled to the tulip (e.g., for use in securing the rod therein). In some examples, the instrument 200 may include or be used with an indicator that indicates a position of the rod in order to ensure that the rod is reduced before coupling the locking cap to the tulip.

In some examples, the inner shaft 210 and cap pusher 212 may be configured to simultaneously engage the rod and locking cap, respectively. For example, the inner shaft 210 may be extended through an opening in the locking cap to directly contact the rod, and the distal end 104 of the inner shaft 210 may be longitudinally spaced or offset from the distal end 104 of the cap pusher 212, such that the inner shaft 210 and cap pusher 212 are configured to contact the rod and locking cap, respectively. In some examples, the instrument 200 may include one or more biasing members 214 (e.g., springs) that absorb or mitigate a force applied to the locking cap (e.g., by the cap pusher) during rod reduction. The biasing members 214 may be housed, for example, in a concealing cap 216 coupled to the inner shaft 210. The concealing cap 216 may include an opening sized, shaped, and/or configured to allow the inner shaft 210 and cap pusher 212 to extend longitudinally therethrough. In some examples, a retaining ring 218 may be positioned at a distal portion of the inner shaft 210 to facilitate keeping the locking cap retained to the instrument 200. The retaining ring 218 may be coupled to the distal portion of the inner shaft 210, for example, via a friction fit.

As shown in FIGS. 7 and 8, the instrument 200 may include a threaded sleeve 220 mounted on or coupled to a proximal portion of the inner shaft 210. The inner shaft 210 is free to rotate and/or translate independent of the threaded sleeve 220. The threaded sleeve 220 may be sized, shaped, and/or configured to engage a shoulder 222 of the inner shaft 210 for use in moving or urging the inner shaft 210 in the distal direction (e.g., in a positive Y-direction). In some examples, a washer 224 may be positioned longitudinally between the inner shaft 210 and threaded sleeve 220 to facilitate reducing friction and/or distributing forces applied therebetween.

A driver nut 230 may be coupled to the distal end 104 of the threaded sleeve 220 for use in rotating the threaded sleeve 220. The driver nut 230 may urge the threaded sleeve 220 to rotate about the longitudinal axis. A coupling mechanism 232 may be used to couple the driver nut 230 to the threaded sleeve. The coupling mechanism 232 may be, without limitation, an assembly screw.

FIGS. 9 and 10 show another example instrument 240 that may be used to reduce a rod and/or insert a locking cap on a screw. As can be understood from a comparison of FIGS. 7 and 8 with FIGS. 9 and 10, the instrument 240 shown in FIGS. 9 and 10 is substantially similar to the instrument 200 shown in FIGS. 7 and 8, except, as shown in FIG. 10, the inner shaft 250 of the instrument 240 includes one or more keyed features 252 at a radially outer surface thereof. The keyed features 252 may be configured to engage a radially-inner surface of a screw tower (e.g., screw tower 100 or 160). For example, as shown in FIG. 11, a screw tower 100 may include one or more keyed features 254 that complement the keyed features 252 of the instrument 240. In this manner, the keyed features 252 and 254 may engage each other when the inner shaft 250 extends through the channel 110 of the screw tower 100. The keyed features 252 and 254 provide anti-rotation properties by mating with the screw tower 100. This in turn restricts or prevents cross threading of the driver nut 230 (e.g., under heavy reduction loads).

FIGS. 12-14 show a selective thread engagement housing 300 that may be used to selectively move and/or position the screw tower 100 and/or instrument 200. In some examples, the housing 300 includes an opening sized, shaped, and/or configured to receive the proximal end 108 of the screw tower 100. The housing 300 may include one or more retention members or tower clips 310 configured to selectively engage or clamp to a proximal portion of the screw tower 100. In some examples, each tower clip 310 is pivotable about a respective rod 312 to move between an engaged position, in which a portion of the tower clip 310 (e.g., a ridge or lip) engages an outer surface of the screw tower 100 to facilitate preventing or restricting the screw tower 100 and housing 300 from moving longitudinally relative to each other, and a disengaged position, in which the portion of the tower clip 310 is spaced from the screw tower 100 such that the screw tower 100 and housing 300 are free to move longitudinally relative to each other.

The housing 300 may include a threaded button 320 configured to engage or mate with the threaded sleeve 220 of the instrument 200. The threaded button 320 may include, for example, an opening 322 sized, shaped, and/or configured to receive the threaded sleeve 220 therethrough. In some examples, the opening 322 may be at least partially defined by a threaded wall 324. In this manner, a driving force of rod reduction may be accomplished by selectively rotating the threaded sleeve 220 while the housing 300 is rigidly secured to the screw tower 100 (e.g., via the tower clips 310) and threadably coupled to the instrument 200 (e.g., via the threaded sleeve 220).

In some examples, the threaded button 320 may be moved transversely across the housing 300 to allow for variable reduction. For example, moving the threaded button 320 in a first transverse direction (e.g., radially outward) may cause the threaded wall 324 to engage an outer surface of the threaded sleeve 220 such that the threaded sleeve 220 may move in the distal direction by rotating about the longitudinal axis in a first direction (e.g., a clockwise direction) and/or move in the proximal direction by rotating about the longitudinal axis in a second direction opposite the first direction (e.g., a counterclockwise direction). On the other hand, moving the threaded button 320 in a second transverse direction (e.g., radially inward) may cause the threaded wall 324 to be spaced from the threaded sleeve 220 such that the instrument 200 and housing 300 are free to move relative to each other (e.g., for rapid adjustment).

As shown in FIG. 14, the housing 300 may include one or more biasing members 328 (e.g., springs) that urge the tower clips 310 and/or threaded button 320 toward the engaged position, thereby supporting or promoting mechanical threaded reduction via rotation of the threaded sleeve 220. Additionally or alternatively, a button pin 326 may be positioned to prevent or restrict the threaded button 320 from moving in the second transverse direction (e.g., toward a disengaged position). Moreover, to facilitate preventing or restricting the threaded button 320 from moving in the second transverse direction during heavy reduction loads, a proximal portion of the threaded button 320 may include a shallow ledge configured to engage or catch on an outer surface of the housing 300 when a heavy reduction load is applied. In some examples, the threaded wall 324 may include a square thread profile that facilitates increasing axial force (e.g., for use in rod reduction) and/or reducing friction between the threaded wall 324 and the outer surface of the threaded sleeve 220 (e.g., when the threaded button 320 is moved in a transverse direction).

The housing 300 may be clipped onto the screw tower 100 before the instrument 200 is inserted into the housing 300, or clipped onto the screw tower 100 with the instrument 200 already extending at least partially through the housing 300. In some examples, the housing 300 may include or be coupled to a counter-torque instrument, a compressor/distractor instrumentation, and/or other tower manipulation instrumentation.

Figure 15:
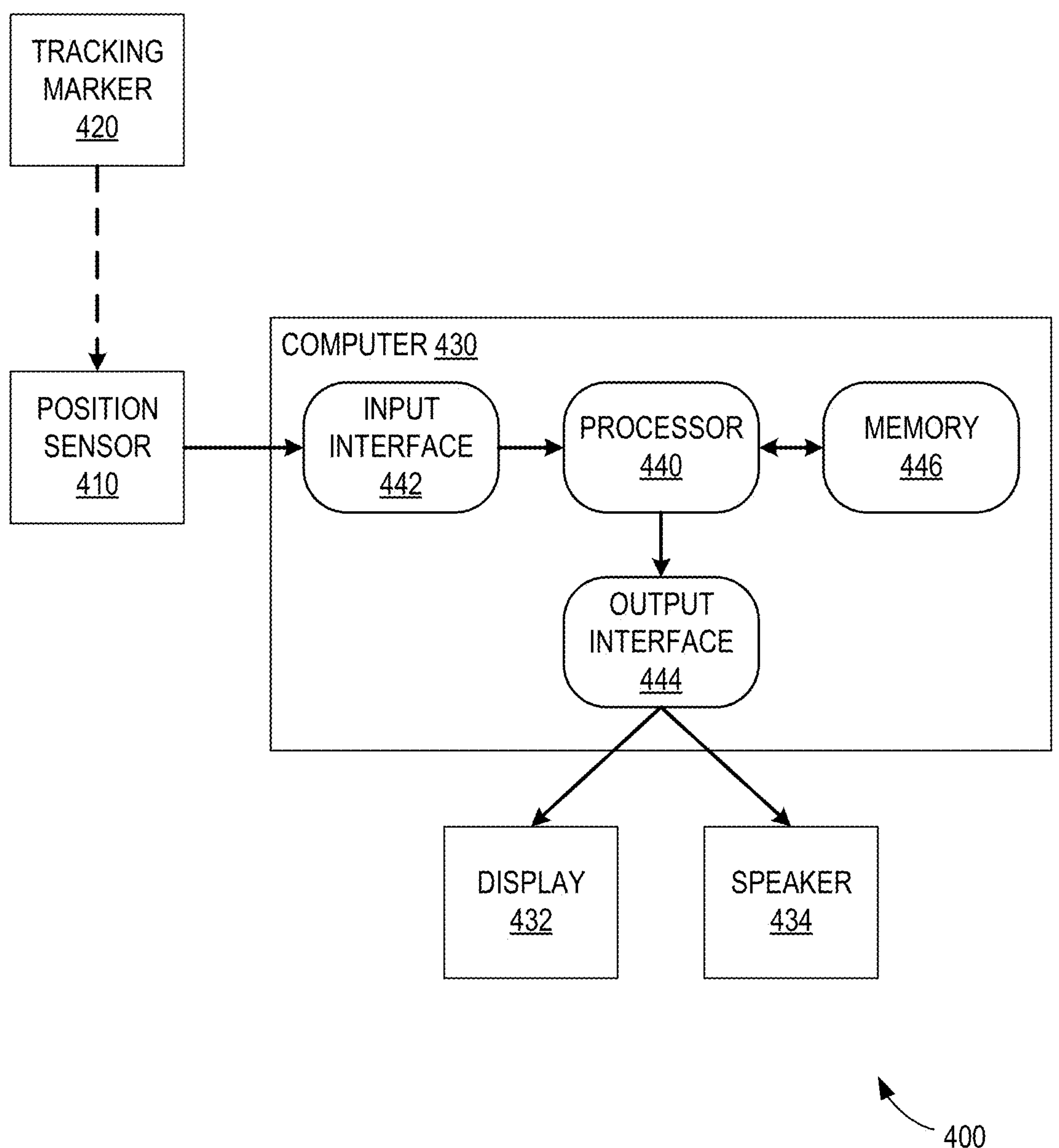
FIG. 15 is a block diagram of an example tracking system that may be used to track one or more objects, such as the screw tower shown in FIG. 1 or 5, the instrument shown in FIG. 7 or 9, and/or the housing shown in FIG. 12.

FIG. 15 shows an example tracking system 400 that may be used to track one or more objects, such as the screw tower 100, instrument 200, and/or housing 300. The system 400 includes one or more position sensors 410 that may be positioned and/or oriented to have a direct line of sight to a surgical field. In some examples, a position sensor 410 may be positioned on a stand configured to move, orient, and support the position sensor 410 in a desired position and/or orientation. The position sensors 410 may include any suitable camera (e.g., an infrared camera, a bifocal camera, a stereophotogrammetric camera, etc.) configured to scan a given measurement volume and detect light and/or other electromagnetic wave that comes from a plurality of tracking markers 420 in order to determine a position of the tracking markers 420 in the given measurement volume.

In some examples, the tracking markers 420 may be mounted or otherwise secured to an object to be tracked during a surgical procedure (e.g., screw tower 100, instrument 200, housing 300). Such objects may include, without limitation, a robot (e.g., at an end-effector), a surgical tool, and/or a patient tracking device secured directly to a patient. In some examples, electromagnetic waves coming from the tracking markers 420 may be detected over time in order to monitor a position and/or movement of one or more marked objects (e.g., an object having tracking markers 420 coupled thereto).

Tracking markers 420 may serve as unique identifiers that are trackable in three dimensions (e.g., using stereophotogrammetry). Tracking markers 420 may include active tracking markers (e.g., infrared light emitting diodes (LEDs)) that are activated by an electrical signal to emit light and/or other electromagnetic wave, and/or passive tracking markers (e.g., retro-reflective markers) that reflect light and/or other electromagnetic wave emitted by an illuminator on the position sensor 410 or other suitable device. In some examples, the tracking markers 420 may include reflective, radiopaque, and/or optical markers. The tracking markers 420 may be suitably shaped, including spherical, spheroid, cylindrical, cube, cuboid, or the like.

A computer 430 may receive and process information from the position sensors 410 in order to present information to a user using a display 432 and/or a speaker 434. In some examples, the computer 430 may include a processor circuit 440 (also referred to as a processor) coupled with an input interface circuit 442 (also referred to as an input interface), an output interface circuit 444 (also referred to as an output interface), and/or a memory circuit 446 (also referred to as a memory). The memory 446 may include computer readable program code that when executed by the processor 440 causes the processor 440 to perform operations according to embodiments disclosed herein. According to other examples, the processor 440 may include memory so that a separate memory circuit (e.g., memory 446) is not required.

The processor 440 may receive input through the input interface 442, and/or provide output through the output interface 444. For example, the processor 440 may receive position sensor data associated with one or more tracking markers 420 from the position sensor 410 through the input interface 442, and/or present position information to the user using the display 432 and/or speaker 434 through input interface 442. In some examples, the position and/or orientation of a marked object may be presented to the user in relation to a three-dimensional image of a patient's anatomical structure.

Figures 16, 17:
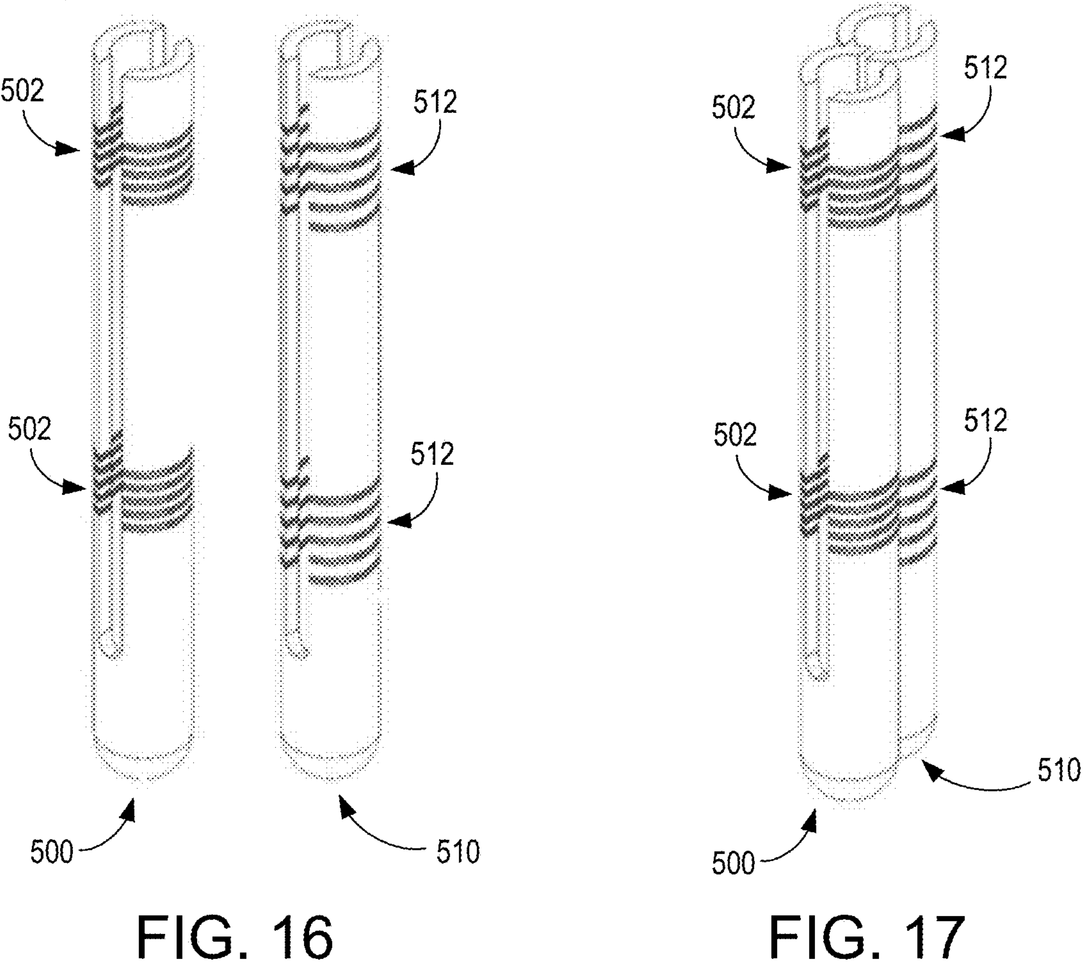
FIG. 16 is a perspective view of example objects that may be tracked, including example tracking markers.
FIG. 17 is a perspective view of the objects shown in FIG. 16 in a partially overlapping arrangement.
Figure 18:
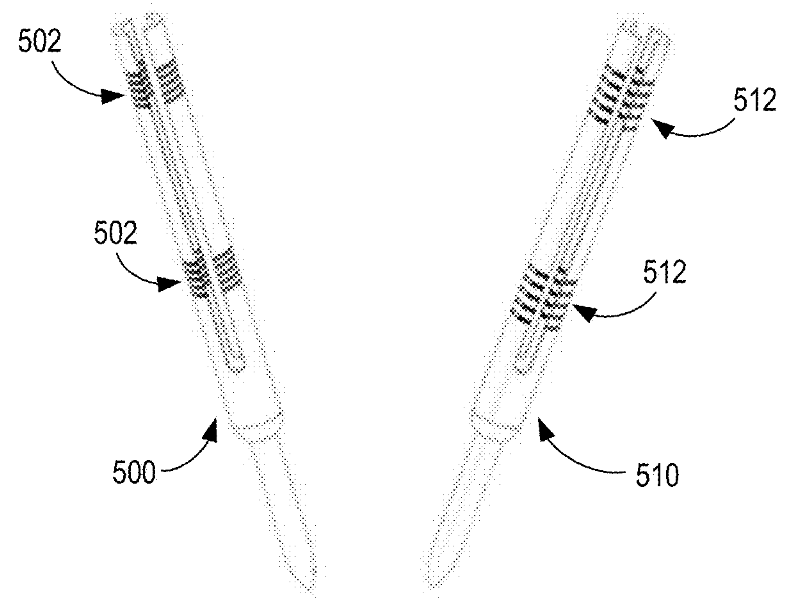
FIG. 18 is a perspective view of the objects shown in FIG. 16 in an example use arrangement.

FIGS. 16-18 show an example first object 500 marked with an example first cluster of stripes 502 and an example second object 510 marked with an example second cluster of stripes 512. In some examples, the computer 430 may be configured to discern between tracking markers 420 (e.g., first cluster of stripes 502, second cluster of stripes 512) by distinguishing inter-stripe spacing (e.g., longitudinal spacing between stripes of a cluster). For example, the first cluster of stripes 502 has a first inter-stripe spacing, and the second cluster of stripes 512 has a second inter-stripe spacing larger than the first inter-stripe spacing.

Each object may be marked at a plurality of locations. For example, the first cluster of stripes 502 is present in two different locations of the first object 500, and the second cluster of stripes 512 is present in two different locations of the second object 510. In some examples, the computer 430 may be configured to discern between objects (e.g., first object 500, second object 510) by distinguishing marker types and inter-cluster spacing (e.g., longitudinal spacing between clusters). For example, the first object 500 has a first inter-cluster spacing, and the second object 510 has a second inter-cluster spacing larger than the first inter-cluster spacing.

The first cluster of stripes 502 and second cluster of stripes 512 may each be configured to uniquely identify a respective object (e.g., first object 500 and second object 510, respectively). For example, the computer 430 may be configured to recognize the first object 500 based on the first cluster of stripes 502 and/or the second object 510 based on the second cluster of stripes 512.

When searching tracked frames for tracking markers 420, the computer 430 may compare the tracked frames to a geometrical model of the cluster of stripes (e.g., first cluster of stripes 502, second cluster of stripes 512), treating the cluster of stripes as a unique marker. Because the computer 430 is searching for a match to a plurality of parameters including cylindrical shape of predetermined diameter and stripes of a predetermined curvature in a sequence of a predetermined number (e.g., five) spanning a predetermined longitudinal length, the computer 430 may find a match and locate its center even if a portion of the object is partially blocked as shown in FIG. 17. That is, the different inter-stripe spacing and/or inter-cluster spacing allows the computer 430 to easily discern between tracking markers 420 and/or objects while also finding accurate locations. For example, on second object 510 as shown in FIG. 17, the comparison to the geometrical model may consider the curvature of the visible stripes and determine that the visible portion of the tracking markers 420 represents the right half of the tracking markers 420. In this manner, example approaches described herein may allow different elements to be distinguished from each other, despite close proximity or partial overlap.

In some examples, a plurality of trackable objects (e.g., first object 500 and second object 510) may be used to form a dynamic reference base (DRB) that is attached to a patient and/or serves as a reference to which other tracked objects are related. To make an object into a navigated element, it may be shaped or marked in unique ways. In one embodiment, an object may have contrasting (e.g., black and white) stripes painted on its shaft, or have slight variances in diameter such that sections are elevated or recessed and appear as stripes, with spacing between stripes being a consistent amount. For example, the spacing between stripes may be 1 millimeter (mm) in one element and 2 mm in another element. A section or group of stripes may have a predetermined number of total stripes so that the computer 430 may localize an exact longitudinal position of the stripe cluster, providing accuracy along and normal to the shaft of the element. If position sensors 410 track a plurality of elements simultaneously, the different stripe spacing allows the computer 430 to distinguish between elements. In other words, the frequency of the stripes may identify a tracking marker 420 from other tracking markers 420 and the cluster of stripes may provide the coordinates of the tracking marker 420.

Figure 19:
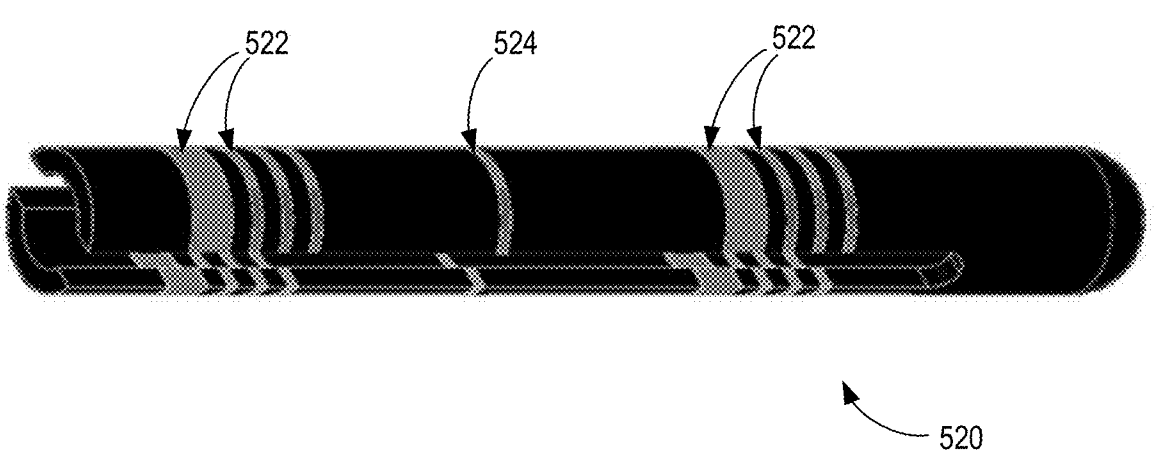
FIG. 19 is a perspective view of another example object that may be tracked, including example tracking markers.

FIG. 19 shows an object 520 with stripes 522 of different thicknesses, a single stripe 524 between clusters of stripes 522, and a contrast of a dark object 520 against white or silver stripes 522 and 524 (e.g., retro-reflective tape). In some embodiments, unique identification of objects 520 may be a function of stripe frequency and/or stripe thickness. Additionally or alternatively, a stripe 524 between clusters may facilitate improving tracking accuracy and/or localization robustness. The color configuration shown in FIG. 19 may facilitate increasing contrast in surgical environments while visually separating the object 520 from the background. Applying localized colors such as red, green, and/or blue to an object 520 may also provide additional feedback to surgeons and/or systems. The example approaches described herein have the advantage of encoding more information and being compatible with existing discrete and continuous linear barcode design principles. Additionally, the example approaches allow implanted hardware (e.g., screw tower 100, instrument 200, housing 300) to serve as a navigated array, allowing registration to be transferred sequentially as additional screws as placed and maintaining better accuracy.

Figure 20:
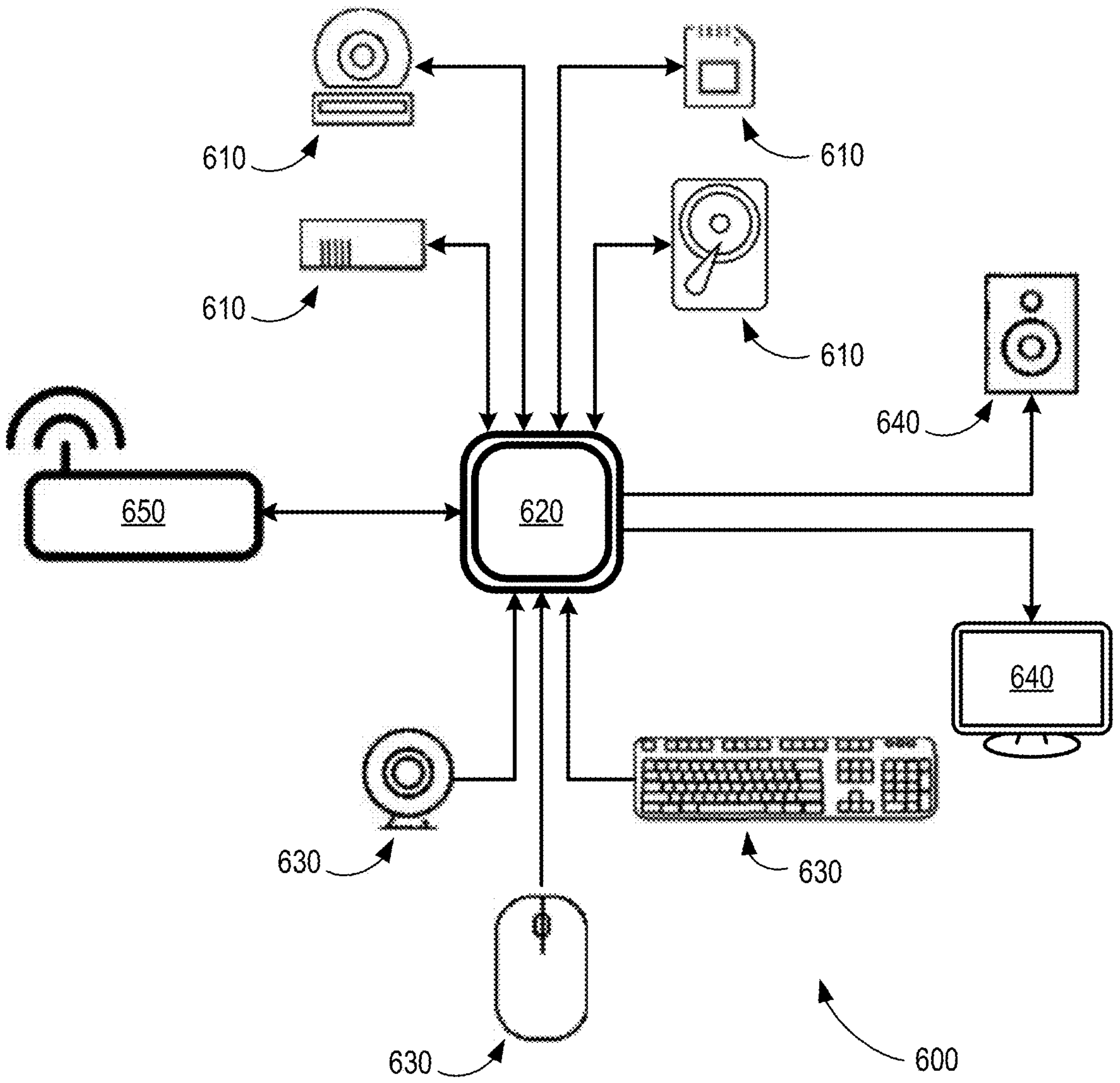
FIG. 20 is a block diagram of an example computing system that may be used to track one or more objects, such as the screw tower shown in FIG. 1 or 5, the instrument shown in FIG. 7 or 9, and/or the housing shown in FIG. 12.

FIG. 20 shows an example computing system 600 configured to perform one or more computing operations. While some examples of the disclosure are illustrated and described herein with reference to the computing system 600 being a computer 430 (shown in FIG. 15) and/or being used with a computer 430, aspects of the disclosure are operable with any computing system (e.g., position sensor 410) that executes instructions to implement the operations and functionality associated with the computing system 600. The computing system 600 shows only one example of a computing environment for performing one or more computing operations and is not intended to suggest any limitation as to the scope of use or functionality of the disclosure.

In some examples, the computing system 600 includes a system memory 610 (e.g., computer storage media) and a processor 620 coupled to the system memory 610. The processor 620 may include one or more processing units (e.g., in a multi-core configuration). Although the processor 620 is shown separate from the system memory 610, examples of the disclosure contemplate that the system memory 610 may be onboard the processor 620, such as in some embedded systems.

The system memory 610 stores data associated with one or more users, tracked objects, position sensors 410, and/or tracking markers 420, and computer-executable instructions, and the processor 620 is programmed or configured to execute the computer-executable instructions for implementing aspects of the disclosure using, for example, the computer 430. The system memory 610 includes one or more computer-readable media that allow information, such as the computer-executable instructions and other data, to be stored and/or retrieved by the processor 620.

By way of example, and not limitation, computer-readable media may include computer storage media and communication media. Computer storage media are tangible and mutually exclusive to communication media. For example, the system memory 610 may include computer storage media in the form of volatile and/or nonvolatile memory, such as read only memory (ROM) or random access memory (RAM), electrically erasable programmable read-only memory (EEPROM), solid-state storage (SSS), flash memory, a hard disk, a floppy disk, a compact disc (CD), a digital versatile disc (DVD), magnetic tape, or any other medium that may be used to store desired information that may be accessed by the processor 620. Computer storage media are implemented in hardware and exclude carrier waves and propagated signals. That is, computer storage media for purposes of this disclosure are not signals per se.

A user or operator may enter commands and other input into the computing system 600 through one or more input devices 630 coupled to the processor 620. The input devices 630 are configured to receive information. Example input device 630 include, without limitation, a pointing device (e.g., mouse, trackball, touch pad, joystick), a keyboard, a game pad, a controller, a microphone, a camera, a gyroscope, an accelerometer, a position detector, and an electronic digitizer (e.g., on a touchscreen). Information, such as text, images, video, audio, and the like, may be presented to a user via one or more output devices 640 coupled to the processor 620. The output devices 640 are configured to convey information. Example, output devices 640 include, without limitation, a monitor, a projector, a printer, a speaker, a vibrating component. In some examples, an output device 640 is integrated with an input device 630 (e.g., a capacitive touch-screen panel, a controller including a vibrating component).

One or more network components 650 may be used to operate the computing system 600 in a networked environment using one or more logical connections. Logical connections include, for example, local area networks, wide area networks, and the Internet. The network components 650 allow the processor 620, for example, to convey information to and/or receive information from one or more remote devices, such as another computing system or one or more remote computer storage media. Network components 650 may include a network adapter, such as a wired or wireless network adapter or a wireless data transceiver.

Figure 21:
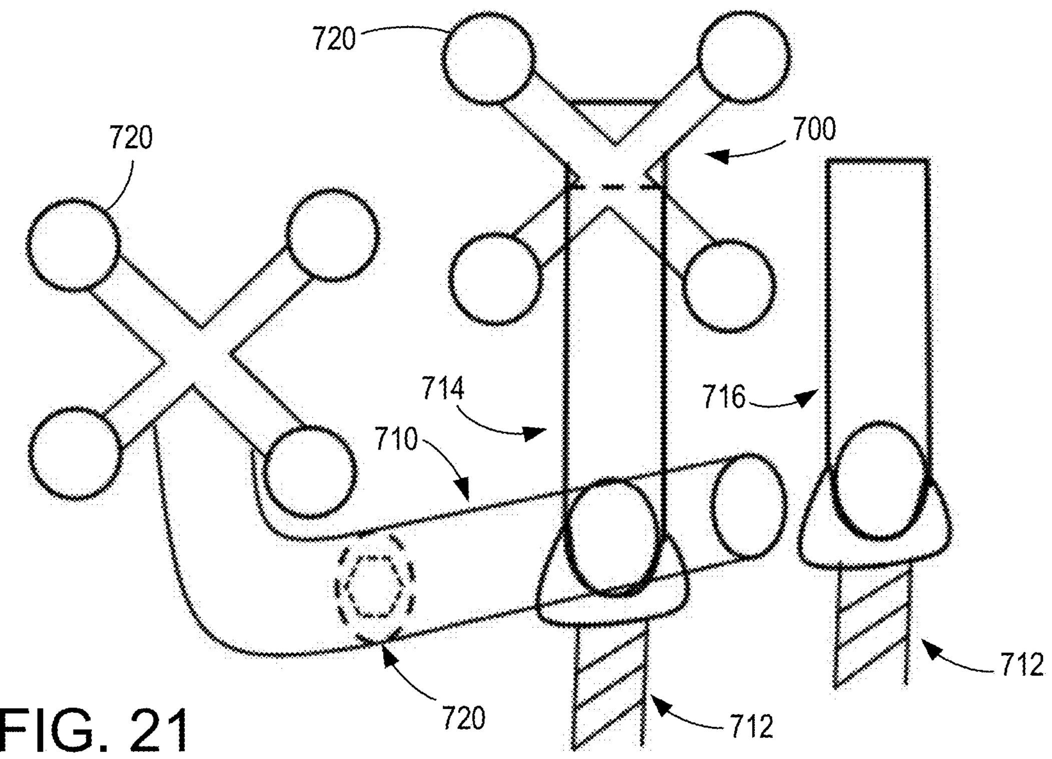
FIG. 21 is a schematic illustration of an example tracking array and navigation array-equipped rod in a first phase in which the tracking array is coupled to a first screw tower and the navigation array-equipped rod extends through the first screw tower.
Figure 22:
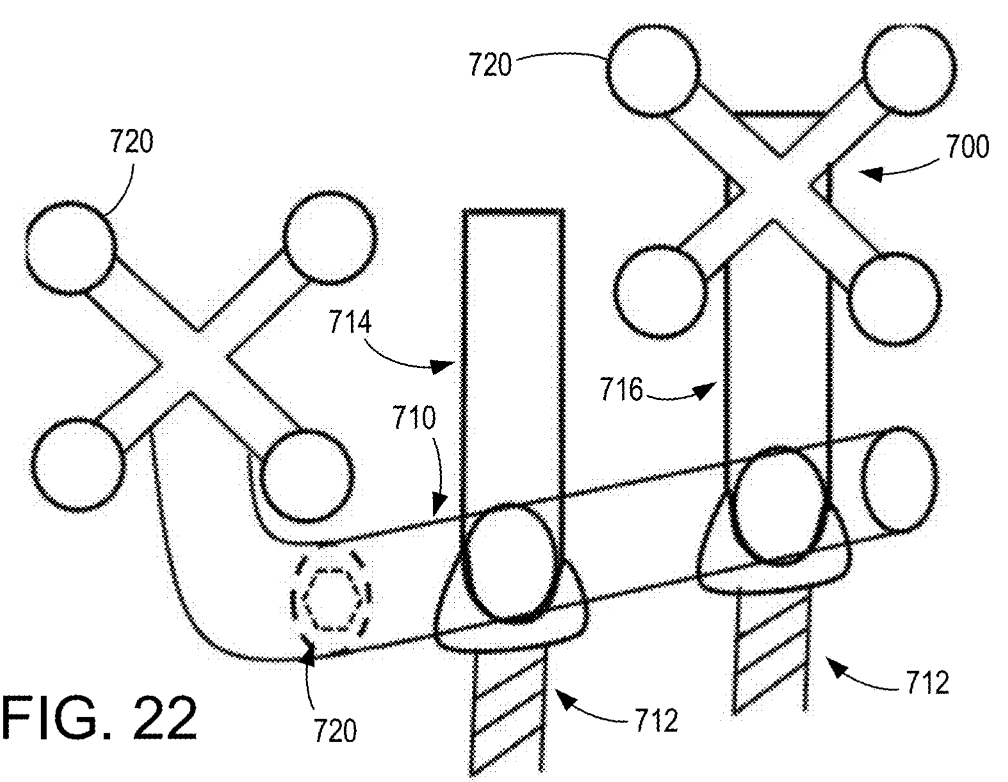
FIG. 22 is a schematic illustration of the tracking array and navigation array-equipped rod shown in FIG. 21 in a second phase in which the tracking array is coupled to a second screw tower and the navigation array-equipped rod extends through the first and second screw towers.

The examples described herein facilitate reducing the amount of soft tissue damage during surgery (e.g., orthopedic spine and neurosurgery), which may lead to less pain, quicker recovery times, and/or lower likelihoods of infection. For example, FIG. 21 shows percutaneous screws FIGS. 21 and 22 show an example tracking array 700 and a navigation array-equipped rod 710 extending transversely across an upper portion of one or more screws 712 (e.g., a tulip of a pedicle screw) and one or more screw towers (e.g., screw tower 100 or 160) coupled to the upper portion of the screws 712. As shown in FIG. 21, the tracking array 700 may be coupled to a first screw tower 714 in a first phase. Once the rod 710 is extended through the first screw tower 714, the tracking array 700 may be uncoupled from the first screw tower 714 and coupled to a second screw tower 716 in a second phase as shown in FIG. 22.

Figure 23:
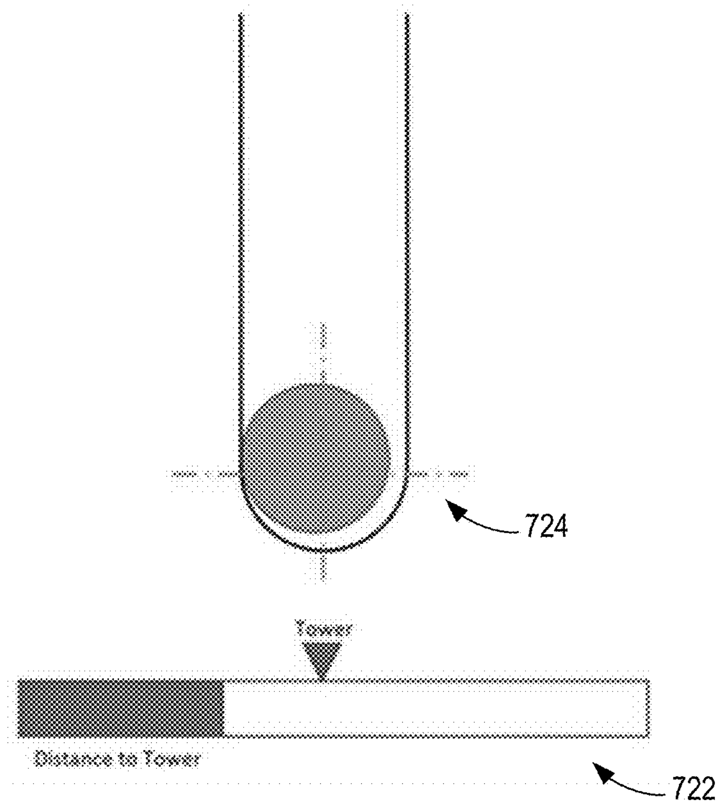
FIG. 23 is a schematic illustration of an example visual aid for use in positioning one or more objects, such as the navigation array-equipped rod shown in FIGS. 21 and 22.

The tracking array 700 and rod 710 each include a plurality of markers 720 that may be tracked (e.g., using position sensors 410) during the first and second phases to enable the relative positions of the rod 710 and first screw tower 714 to be determined (e.g., using the computer 430). In this manner, the rod 710 may be extended through the first screw tower 714 and second screw tower 716 using feedback from the tracking system 400. For example, as shown in FIG. 23, the display 432 may aid in positioning the rod 710 by showing a distance 722 to the first screw tower 714 or second screw tower 716 and an alignment 724 of the rod 710 relative to an opening defined in the first screw tower 714 or second screw tower 716 (e.g., longitudinal channel 138). While FIGS. 21-22 show the tracking array 700 and rod 710 each including a plurality of arms and a spherical marker at an end portion of each arm, the tracking array 700 and/or rod 710 may include one or more tracking markers 420 for tracking the rod 710, screws 712, first screw tower 714, and/or second screw tower 716.

Figure 24:
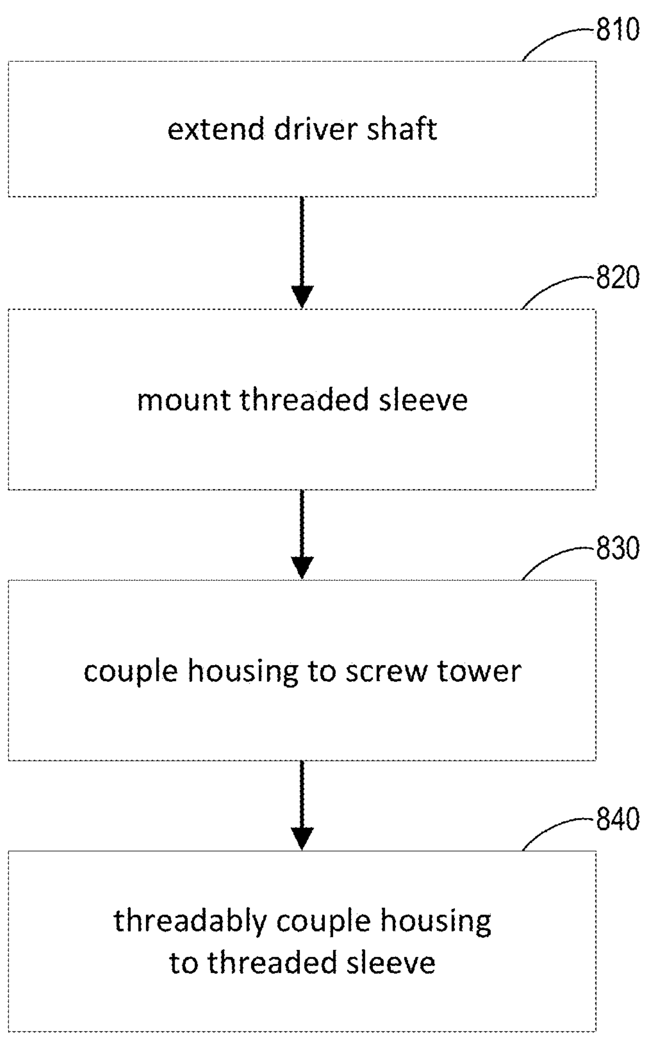
FIG. 24 is a flow chart of an example method of providing a rod reduction tool in accordance with one example of the inventive subject matter.
Figure 25:
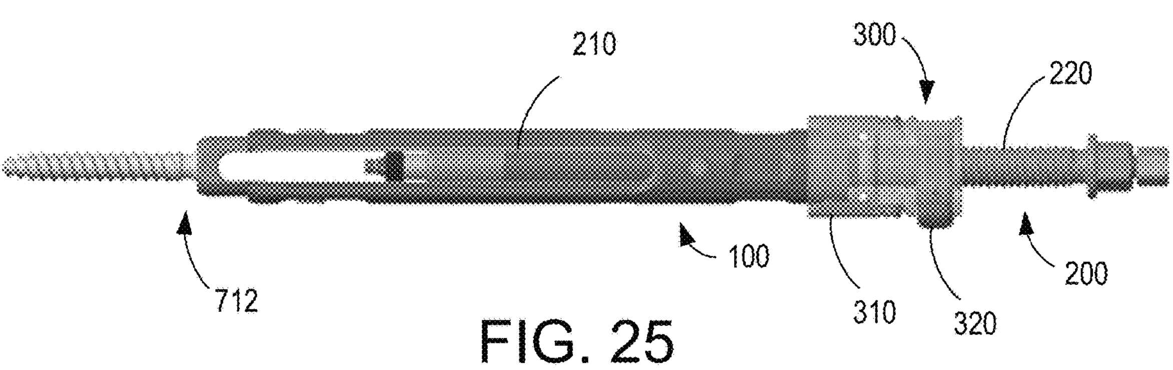
FIG. 25 is a front view of an assembly including a pedicle screw, a screw tower, such as the screw tower shown in FIG. 1 or 5, an instrument, such as the instrument shown in FIG. 7 or 9, and a housing, such as the housing shown in FIG. 12.
Figure 26:
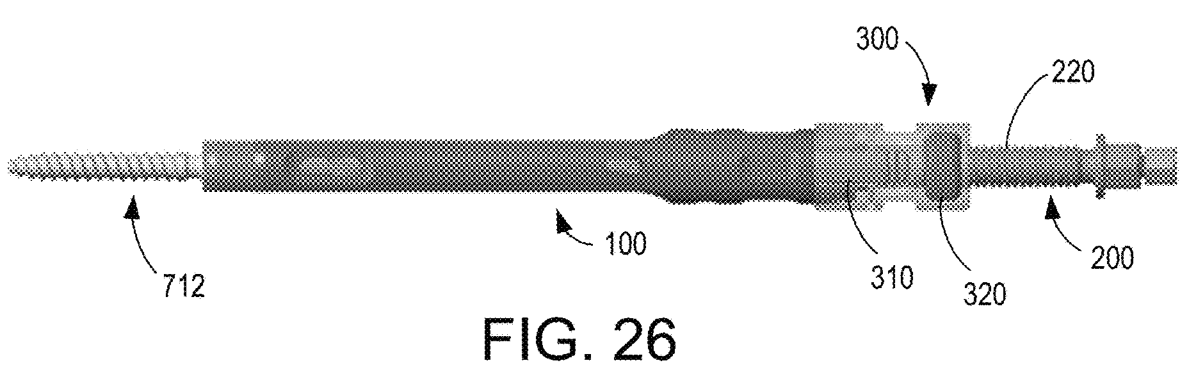
FIG. 26 is a side view of the assembly shown in FIG. 25.
Figure 27:
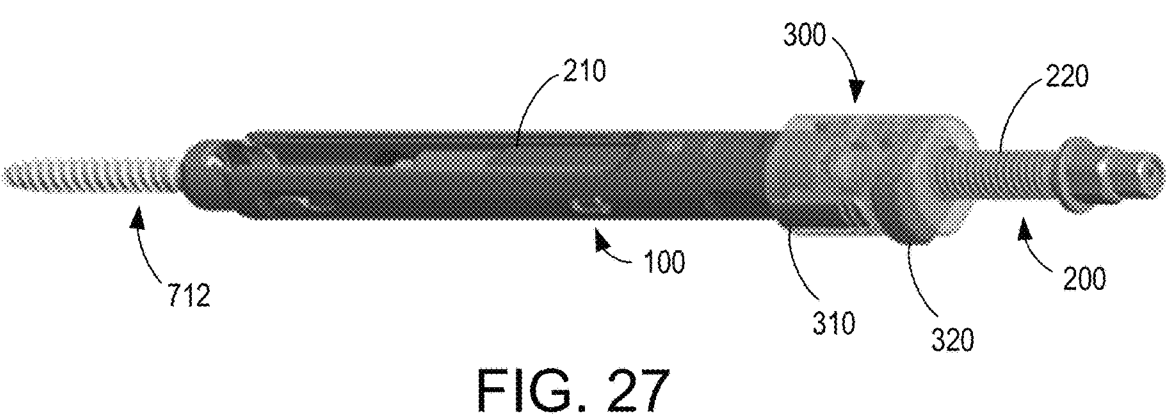
FIG. 27 is a perspective view of the assembly shown in FIG. 25.

FIG. 24 shows an example method 800 of providing a rod reduction tool. As shown in FIGS. 21 and 22, the rod 710 may extend transversely across an upper portion of a screw 712 and a screw tower (e.g., screw tower 100 or 160) coupled to the upper portion of the screw 712. As shown in FIGS. 25-27, the screw tower 100 may be rigidly and/or robustly coupled to the screw 712 to allow for screw manipulation or compression/distraction. In some examples, a driver shaft (e.g., inner shaft 210) is extended longitudinally through the screw tower 100 at operation 810. For example, a distal end 104 of the driver shaft may be inserted into the proximal opening 106 of the screw tower 100 and moved in the distal direction. A threaded sleeve 220 may be mounted on a proximal portion of the driver shaft at operation 820 to form the instrument 200.

A housing 300 may be coupled to the screw tower 100 using one or more retention members (e.g., tower clips 310) at operation 830. The housing 300 may be threadably coupled to the threaded sleeve 220 using a threaded button 320 at operation 840. The threaded sleeve 220 is rotatable about a longitudinal axis to urge the driver shaft longitudinally relative to the screw tower 100. The driver shaft being able to protrude through a locking cap allows the instrument 200 to achieve rod reduction without putting extraneous force on the locking cap, thereby mitigating a likelihood of premature damage to the locking cap and/or tulip. In some examples, the screw tower 100, instrument 200, and/or housing 300 may be marked and used as locating and/or guidance devices for inserting interconnecting rods.

The previously mentioned examples allow for quick and robust connection to a bone screw and tulip and also allows for reduction instrumentation to connect within a small footprint. The internal variable reduction is not only robust, but also does keeps the outer diameter of the screw tower slim, minimizing the incision size. The following instrumentation may also function with other instrumentation to allow for other technique related steps including but not limited to: rod measuring, rod passage, rod reduction, locking cap attachment and tightening, compression, and distraction. The following embodiments represent an approach that may be used to hold a pedicle screw to a tower-based instrument; a tube-based device allowing rod passage, rod reduction, and locking cap delivery and tightening following screw implantation. Reduction embodiments may allow for free moving reduction followed by mechanically assisted reduction to save time by allowing particular orientations or intermittent functionality of certain internal components not possible in all minimally invasive screw instrumentation systems. Additionally, the potential ability to use instrumentation from other currently available Globus systems may reduce the number of sets required in the operating room, may streamline the procedure, and may also reduce operating room time due to a potentially more streamlined technique.

This written description uses examples to disclose aspects of the disclosure and also to enable a person skilled in the art to practice the aspects, including making or using the above-described systems and executing or performing the above-described methods. Having described aspects of the disclosure in terms of various examples with their associated operations, it will be apparent that modifications and variations are possible without departing from the scope of the disclosure as defined in the appended claims. That is, aspects of the disclosure are not limited to the specific examples described herein, and all matter contained in the above description and shown in the accompanying drawings shall be interpreted as illustrative and not in a limiting sense. For example, the examples described herein may be implemented and utilized in connection with or applied to other examples and applications without departing from the scope of the disclosure. Thus, the aspects of the disclosure are not intended to be limited to the above description and/or accompanying drawings, but are to be accorded the broadest scope consistent with the principles and features disclosed herein.

It is to be understood that the present disclosure is not limited in its application to the details of construction and/or the arrangement of components set forth in the description herein or illustrated in the drawings. For example, in accordance with the principles of the disclosure, any feature described herein and/or shown in the drawings may be referenced and/or claimed in combination with any other feature described herein and/or shown in the drawings. Skilled artisans will recognize the examples provided herein have many useful alternatives and fall within the scope of the disclosure.

The teachings of the present disclosure may be used and practiced in other embodiments and practiced or carried out in various ways. For example, components of the systems and/or operations of the methods described herein may be utilized independently and separately from other components and/or operations described herein. Moreover, the methods described herein may include additional or fewer operations than those disclosed, and the order of execution or performance of the operations described herein is not essential unless otherwise specified. That is, the operations may be executed or performed in any order, unless otherwise specified, and it is contemplated that executing or performing a particular operation before, contemporaneously with, or after another operation is within the scope of the disclosure. Moreover, the functionality of a given block of the flowcharts and/or block diagrams may be separated into multiple blocks, and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction to the depicted arrows.

It should be apparent from the foregoing description that one or more block diagrams described herein may represent conceptual views of illustrative circuitry embodying the principles of the disclosure and that various examples may be implemented in hardware and/or as computer program instructions stored on a non-transitory machine-readable storage medium. Computer program instructions may be provided to a processor of a general purpose computer circuit, a special purpose computer circuit, and/or other programmable data processing circuit to produce a machine, such that the instructions, which execute via the processor, transform and control transistors, values stored in memory locations, and other hardware components within such circuitry to perform the operations described in detail herein, including the functions/acts associated with the blocks of the flowcharts and/or block diagrams, and thereby create means (functionality) and/or structure for performing such operations. It will be appreciated by those skilled in the art that any flowcharts, sequence diagrams, state transition diagrams, pseudo code, and the like represent various processes that may be substantially represented in machine-readable storage media and so executed by a computer or processor, whether or not such computer or processor is explicitly shown.

Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When introducing aspects of the disclosure or the examples thereof, the articles "a," "an," "the," and "said" are intended to mean that there are one or more of the elements, unless the context clearly indicates otherwise. References to an "embodiment" or an "example" of the present disclosure are not intended to be interpreted as excluding the existence of additional embodiments or examples that also incorporate the recited features. The phrase "one or more of the following: A, B, and C" means "at least one of A and/or at least one of B and/or at least one of C." The term "and/or" includes any and all combinations of one or more of the associated listed items. It will be understood that although ordinal terms (e.g., "first," "second," "third," etc.) may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Also, it is to be understood that the phraseology and terminology used herein is for the purpose of description and should not be regarded as limiting. Use of the terms "including," "comprising," or "having," and variations thereof, herein is meant to encompass the items listed thereafter and equivalents thereof, as well as additional items. Unless specified or limited otherwise, the terms "mounted," "connected," "supported," and "coupled," and variations thereof, are used broadly and encompass both direct and indirect mountings, connections, supports, and couplings. Further, "connected" and "coupled" are not restricted to physical or mechanical connections or couplings. Moreover, when an element is referred to as being "connected," "coupled," or "responsive," and variations thereof, to another element, it can be directly connected, coupled, or responsive to the other element or intervening elements may be present. In contrast, when an element is referred to as being "directly connected," "directly coupled," or "directly responsive," and variations thereof, to another element, there are no intervening elements present. Furthermore, "connected," "coupled," "responsive," or variants thereof as used herein may include wirelessly coupled, connected, or responsive.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A rod reduction system for use with a tracking system comprising:
- a screw tower having:
  - an outer sleeve having distal ends adapted to mate to an exterior feature of a tulip of a bone screw, the outer sleeve further having extensions extending radially inwardly; and
  - an inner sleeve configured to be slidably coupled to the outer sleeve and configured to secure the bone screw to the outer sleeve, the inner sleeve having longitudinal slots for receiving the extensions of the outer sleeve to prevent rotation of the inner sleeve relative to the outer sleeve;
- a driver having a shaft extendable longitudinally through the screw tower, the shaft having a threaded sleeve disposed around a proximal portion of the shaft; and
- a housing configured to attach to the screw tower and holding a threaded insert configured to threadably couple to the threaded sleeve of the shaft, wherein the threaded sleeve is rotatable about a longitudinal axis to urge the driver shaft longitudinally relative to the screw tower to reduce a rod disposed in the tulip,
- a tracking system for use with a robot including:
- a computer, a display in communication with the computer;
- a position sensor in communication with the computer;
- one or more tracking markers disposed on the screw tower;
- wherein the position sensor is configured to detect the one or more tracking markers to determine position sensor data of the one or more tracking markers;
- wherein the computer is configured to receive the position sensor data and present the position of the screw tower via the display in relation to an image of an anatomical structure of a patient.

2. The system of claim 1, wherein the housing includes retention clips configured to clamp to external features disposed in a proximal portion of the screw tower.

3. The system of claim 2, wherein each retention clip includes a spring loaded pivoting clip biased to a clamped position.

4. The system of claim 1, wherein the threaded insert includes a threaded button having a threaded hole configured to threadably couple to the threaded sleeve, the button switchable between an engaged position for engaging with the threaded sleeve and a disengaged position.

5. The system of claim 4, wherein the threaded button is a spring loaded threaded button biased to the engaged position.

6. The system of claim 4, wherein the threaded button is a transversely movable spring loaded threaded button biased to the engaged position, wherein transverse movement of the threaded button against the bias releases the threaded engagement with the threaded sleeve.

7. The system of claim 1, wherein the system includes a second screw tower positioned on a second location on the patient, and one or more tracking markers disposed on the second screw tower.

8. The system of claim 1, wherein the one or more tracking markers are passive tracking markers.

9. The system of claim 1, further comprising a robot trackable by the position sensor.

10. The system of claim 1, further comprising a surgical tool trackable by the position sensor.

11. A rod reduction system for use with a tracking system comprising:
- a computer;
- a screw tower configured to be positioned at a first location on a patient during the surgical procedure;
- a position sensor in electronic communication with the computer;
- one or more tracking markers positioned on the screw tower;
- wherein the screw tower includes:
  - an outer sleeve having distal ends adapted to mate to an exterior feature of a tulip of a bone screw, the outer sleeve further having extensions extending radially inwardly; and
  - an inner sleeve configured to be slidably coupled to the outer sleeve and having a pair of mating extensions configured to be positioned inside the tulip to sandwich the tulip between the outer sleeve and the inner sleeve, thereby locking the bone screw to the outer sleeve, the inner sleeve having longitudinal slots for receiving the extensions of the outer sleeve to prevent rotation of the inner sleeve relative to the outer sleeve;
- a driver having a shaft extendable longitudinally through the screw tower, the shaft having a threaded sleeve disposed around a proximal portion of the shaft; and
- a housing configured to attach to the screw tower and holding a threaded insert configured to threadably couple to the threaded sleeve of the shaft, wherein the threaded sleeve is rotatable about a longitudinal axis to urge the driver shaft longitudinally relative to the screw tower to reduce a rod disposed in the tulip, wherein the position sensor is configured to detect the one or more first tracking markers to determine position sensor data of the one or more first tracking markers and provide the position sensor data to the computer.

12. The system of claim 11, wherein the housing includes retention clips configured to clamp to external features disposed in a proximal portion of the screw tower.

13. The system of claim 12, wherein each retention clip includes a spring loaded pivoting clip biased to a clamped position.

14. The system of claim 11, further comprising:

a second screw tower positioned at a second location on the patient; and one or more second tracking markers disposed on the second screw tower.

15. The system of claim 14, wherein the one or more first tracking markers and the second one or more tracking markers are passive tracking markers.

16. The system of claim 11, further comprising a robot trackable by the position sensor.

17. The system of claim 11, further comprising a surgical tool trackable by the position sensor.

* * * * *